United States Patent [19]
Osterholt et al.

[11] Patent Number: 6,093,286
[45] Date of Patent: Jul. 25, 2000

[54] PROCESS FOR PURIFYING N-BUTYL CHLORIDE

[75] Inventors: Clemens Osterholt, Dorsten; Josef Metz, Marl; Udo Jegelka, Recklinghausen, all of Germany

[73] Assignee: Huels Aktiengesellschaft, Marl, Germany

[21] Appl. No.: 09/084,957

[22] Filed: May 28, 1998

[30] Foreign Application Priority Data

May 28, 1997 [DE] Germany .......................... 197 22 281
May 7, 1998 [DE] Germany .......................... 198 20 330

[51] Int. Cl.[7] .......................... B01D 11/04; C07C 17/383
[52] U.S. Cl. .............................. 203/44; 203/91; 570/262; 570/263
[58] Field of Search .......................... 203/39, 44, 91–92, 203/95, 100; 570/258, 262, 263; 202/202

[56] References Cited

U.S. PATENT DOCUMENTS 3,654,093  4/1972  Schexnayder et al. ............... 203/8
3,848,005  11/1974  Sullivan ................................. 570/111
5,132,476  7/1992  Osterburg et al. ..................... 570/258
5,371,313  12/1994  Ostrowicki ............................ 585/642

FOREIGN PATENT DOCUMENTS 462993   7/1928   Germany.
0138470  11/1979  Germany.
138470   11/1979  Germany.

*Primary Examiner*—Virginia Manoharan
*Attorney, Agent, or Firm*—Oblon, Spivak, McClelland, Maier, & Neustadt, P.C.

[57] ABSTRACT

A process for purifying at least 90% pure n-butyl chloride which is present in a mixture with other $C_1$ to $C_4$ alkyl chlorides, $C_1$ to $C_4$ alcohols, esters, ketones, nitrites, and organic sulfur compounds. In this process the mixture is first distilled, with high-boilers being separated off, and then washed in a plurality of stages with water and with dilute alkali metal hydroxide solution, and, optionally, an aqueous solution of $H_2O_2$. In this manner, even a typical impurities may be separated off and a >99% pure product may be obtained.

12 Claims, No Drawings

PROCESS FOR PURIFYING N-BUTYL CHLORIDE

BACKGROUND OF THE INVENTION

1. Field of the Invention The present invention relates to a process for purifying at least 90% pure n-butyl chloride which is present in mixtures with other $C_1$ to $C_4$ alkyl chlorides, $C_1$ to $C_4$ alcohols, esters, ketones, nitrites, and organic sulfur compounds, via distillation and washing of the distillate.

2. Description of the Background

Alkyl chlorides are valuable solvents. Furthermore, n-butyl chloride is an important intermediate for preparing a variety of organometallic compounds and crop protection agents and pharmaceutical products.

The preparation of n-butyl chloride generally starts from n-butanol and hydrogen chloride. Minor components which occur in the preparation are butanes, isomeric chlorobutanes, n-butanol and di-n-butyl ether. Therefore, purification processes generally only concern removing these byproducts.

Thus, in EP-B-0,392,270, all of the reaction product of the continuous reaction of $C_3$ to $C_4$ monoalkanols with hydrogen chloride is initially taken off in the vapor state for work-up. The mixture is then cooled, phase separation is induced and the phases are then further worked up separately. The alkyl chloride phase is washed with water, dried and, if appropriate, purified by a two-stage continuous distillation.

In German Patent 462,993, n-butanol is reacted with hydrochloric acid under pressure. The reaction product is washed with soda solution (sodium carbonate solution).

According to DD 138 470, the reaction of n-butanol with hydrochloric acid in a reactor having an attached column is carried out in such a manner that the di-n-butyl ether produced in small amounts as byproduct predominantly remains in the reactor. At the top of the column, a mixture is taken off which predominantly comprises water and n-butyl chloride. After the phase separation, the n-butyl chloride phase is washed in counter-current with weakly alkaline water.

Accordingly, the purification processes described above are essentially restricted to separating off n-butanol, isomeric chlorobutanes and d-in-butyl ether from the desired n-butyl chloride.

SUMMARY OF THE INVENTION

The object of the present invention is to provide a simple process for purifying at least 90% pure n-butyl chloride containing a significantly broader spectrum of minor components as compared to the processes described above. In particular, in the purification, even esters, ketones and nitriles should be able to be separated off in a satisfactory manner.

The object is achieved according to the invention by first distilling the mixtures, with high-boilers being separated off. The distillate is then cooled and washed in a plurality of stages with water and with dilute alkali metal hydroxide solution.

Accordingly, the present invention is accomplished with a process for separating n-butyl chloride from other isomeric $C_4$ alkyl chlorides, $C_1$ to $C_3$ alkyl chlorides, $C_1$ to $C_4$ alcohols, esters, ketones, nitriles, and organic sulfur compounds, by:

distilling a composition containing at least 90% by weight n-butyl chloride, at least one other isomeric $C_4$ alkyl chloride, at least one $C_1$ to $C_3$ alkyl chloride, at least one $C_1$ to $C_4$ alcohol, at least one ester, at least one ketone, at least one nitrile, and at least one organic sulfur compound, to produce a distillate having a higher content of the n-butyl chloride as compared to the composition;

cooling the distillate;

washing the cooled distillate with a dilute solution of an alkali metal hydroxide in water; and washing the cooled distillate with water.

A more complete appreciation of the invention and many of the attendant advantages thereof will be readily obtained as the same becomes better understood by reference to the following detailed description.

DETAILED DESCRIPTION OF THE PREFERRED EMBODIMENTS

The first step of the present process is distilling the impure composition to separate the high boilers from the n-butyl chloride. In the distillation a distillate is produced which has a higher content, based on weight percent, of the n-butyl chloride as compared to the starting impure composition. Also produced in the distillation is a bottoms fractions which contains the high boilers and, possibly, some of the n-butyl chloride as well. After cooling, the distillate is washed with water and a dilute alkali metal hydroxide solution for additional purification.

The impure starting composition contains at least 90% by weight of n-butyl chloride. The n-butyl chloride content of the composition may be higher than 90% by weight, such as 90.5, 91, 91.5, 92, 92.5, 93, 93.5, 94, 94.5, 95, 95.5, 96, 96.5, and 97% by weight, inclusive of all specific values and subranges therebetween.

The process of the present invention for purifying n-butyl chloride is preferably applied to mixtures which, in addition to the n-butyl chloride, also contain:

$\leq 0.2\%$ other isomeric butyl chlorides, $\leq 1\%$ $C_1$ to $C_3$ alkyl chlorides, $\leq 8\%$ $C_1$ to $C_4$ alcohols, $\leq 3\%$ esters, $\leq 3\%$ ketones, $\leq 0.5\%$ nitrites, and $\leq 0.1\%$ organic sulfur compounds, where all quantities are % by weight in this disclosure unless noted otherwise.

In particular, the impure mixtures contain:

92 to 97% n-butyl chloride, $\leq 0.2\%$ other isomeric butyl chlorides, 0.1 to 0.5% $C_1$ to $C_3$ alkyl chlorides, 2 to 6% $C_1$ to $C_4$ alcohols, 0.01 to 2%, preferably 0.2 to 2% esters, 0.01 to 2% ketones 0.01 to 0.1% nitrites, and 0.001 to 0.005 organic sulfur compounds.

Such mixtures may be obtained, e.g., in the manufacture of fine chemicals or plant protection agents.

Examples of the other isomeric $C_1$ to $C_4$ alkyl chlorides present in the mixture, excluding, of course, n-butyl chloride, are chloromethane, methylene chloride, ethyl chloride and the chlorobutanes isomeric to n-butyl chloride.

The mixtures can contain, for example, the alcohols methanol, ethanol, isopropanol, n-butanol, isobutanol or tert-butanol.

Esters which may be present are, for example, $C_3$–$C_7$ esters such as methyl formate, ethyl formate, butyl formate, methyl acetate, butyl acetate and methyl butyrate.

Among the possible ketones, $C_3$–$C_6$ ketones, especially acetone, methyl ethyl ketone and 4-methyl-2-pentanone, may be mentioned.

Representatives of the nitriles are, for example, $C_2$–$C_5$ nitrites, such as acetonitrile and butyronitrile.

Representative organic sulfur compounds are, e.g., methyl mercaptan, ethyl mercaptan, butyl mercaptan, dimethyl thioether, and dimethyl sulfide. Often it is possible to remove sulfur compounds with the use of activated carbon. However, this method does not provide satisfactory results when used with the subject mixtures, i.e., the n-butyl chloride mixtures described initially, supra.

Preferably, the distillation is performed at 50 to 120° C. and at 0.5 to 3 bar. Temperatures of 65 to 90° C. and atmospheric pressure are very particularly preferred in this case. These temperature ranges include all specific values and subranges therebetween, including 55, 60, 70, 75, 80, 85, 95, 100, 105, and 115° C. The pressure range includes all specific values and subranges therebetween, including 0.75, 1.0, 1.5, 2.0, and 2.5 bar.

After cooling, the distillate further purified in a plurality of washing steps. After the distillate is cooled, it is preferably washed in 2 to 8, and particularly preferably in 3 to 5, stages with water and dilute alkali metal hydroxide solution, and possibly an aqueous $H_2O_2$ solution. At least one of these washing stages is operated using the alkaline washing medium. The ratio of alkyl chloride phase to washing medium is generally in the range from 1:1 to 1:8, preferably 1:2 to 1:5. The dilute alkali metal hydroxide solution used is preferably a 1 to 5% strength sodium hydroxide solution. The washing steps may be conducted in any order. For example, the cooled distillate may be first washed with water and then with the alkaline medium. Alternatively, the distillate may be washed first with the alkaline medium and then subsequently washed with water. The aqueous $H_2O_2$ solution may be used at a concentration of 1 to 70% wt. %, preferably 1–60 wt. %, more preferably 10–30 wt. %.

After the washing, the alkyl chloride phase is dried. The n-butyl chloride content of this phase is then >99%, generally even >99.5%, and 99.7% or greater. Despite the multiplicity of the byproducts in the impure starting composition, the purification is therefore successful in a very simple manner. In this case the end product may contain <0.2% other $C_1$ to $C_4$ alkyl chlorides, <0.05% $C_1$ to $C_4$ alcohols, <0.02% esters, <0.01% ketones and <0.01% nitrites, and 0.0005% organic sulfur compounds. Preferably, the end product contains <0.1% other $C_1$ to $C_4$ alkyl chlorides, <0.02% $C_1$ to $C_4$ alcohols, <0.01% esters, <0.005% ketones and <0.005% nitrites.

The washing may be carried out countercurrently or cocurrently, using suitable apparatus. The process can be carried out continuously, i.e., the distilling and washing steps are conducted simultaneously, in which case the washing waters can be recycled after work-up. The wash water for the $H_2O_2$ wash may be reused for several wash cycles without being treated, and is then suitably disposed of.

When the process is carried out in practice, the distillation bottom phase, which contains the high-boilers, may be recycled or discharged, depending on the n-butyl chloride content. Generally, when the bottom phase has an n-butyl chloride content of >30%, it is recycled to the distillation column. The washing waters, with the exception of the $H_2O_2$ wash water, are combined and purified by being stripped of organic constituents. They can then be fed to waste water treatment or used again for washing. The stripping column distillate, which predominantly contains alcohols with a small amount of ketones and alkyl chlorides, is concentrated and disposed of.

The distillation may be conducted in any suitable apparatus known in the art. For a general discussion of distillation processes, etc., see *Kirk-Othmer Encyclopedia of Chemical Technology*, Volume 8, pp. 311–358, 1993, incorporated herein by reference.

Having generally described this invention, a further understanding can be obtained by reference to certain specific examples which are provided herein for purposes of illustration only and are not intended to be limiting unless otherwise specified.

EXAMPLES

Example 1

600 g of a crude n-butyl chloride having the composition shown in Table 1 are distilled at atmospheric pressure in a 0.5 m column containing Multifil packings. The reflux ratio is 2:1. This produces 90.5% distillate having an n-butyl chloride content of 97.4% and 9.3% bottom phase having an n-butyl chloride concentration of >70%, the bottom phase being used for a subsequent distillation. The distillation losses are 0.2%=1.2 g.

The distillate is washed 4 times in a round-bottom flask with vigorous stirring. The washing stages 1, 2 and 4 are carried out using demineralized water, and 2% strength sodium hydroxide solution is used for the 3rd wash. The ratio of alkyl chloride phase to the washing water phases is approximately 1:5.

The washing waters of the individual stages are combined, whereupon the organic constituents are separated off in a stripping column.

The purified alkyl chloride phase is dehydrated using NaOH. The n-butyl chloride is thus obtained in a yield of >90%, based on the initial charge. Taking into account the recycling of the distillation bottom phase, a yield of >94% is achieved.

Product data: n-butyl chloride content 99.7% according to GC analysis APHA color index $\leq 15$ $H_2O$ content $\leq 200$ ppm

TABLE 1

|  | Crude product [%] | Purified Product [%] |
|---|---|---|
| n-Butyl chloride | 96.2 | 99.77 |
| Other butyl chlorides | 0.1 | 0.1 |
| $C_4$ alcohols | 1.6 | <0.01 |
| $C_1$ to $C_3$ alkyl chlorides | 0.11 | <0.05 |
| $C_1$ to $C_3$ alcohols | 0.4 | <0.005 |
| Methyl acetate | 0.8 | <0.005* |
| Butyl formate | 0.25 | <0.005 |
| n-Butyl acetate | 0.36 | <0.005 |
| Butanes | 0.044 | <0.03 |
| Di-n-butyl ether | <0.005 | <0.003 |
| Acetonitrile | 0.016 | <0.005 |
| Acetone | 0.02 | <0.01 |
| Organic sulfur compounds | 0.0017 | 0.0005 |
| Unknown residue | 0.11 | 0.01 |
|  | 100.017 | 100.009 |

*If water is used in the 3rd washing stage instead of 2% strength NaOH, the metyl acetate content is 0.027%.

Example 2

The procedure was as in Example 1, except that before the distillate was washed with 2% sodium hydroxide solution, it was further treated with 10% aqueous $H_2O_2$ solution in a ratio of 1:1 by weight. This reduced the content of organic sulfur compounds from 5 ppm to <2 ppm.

In view of the low odor threshold of sulfur-containing compounds, the additional washing with $H_2O_2$ substantially improved the odor characteristics of the product compound.

Obviously, numerous modifications and variations of the present invention are possible in light of the above teachings. It is therefore to be understood that within the scope of the appended Claims, the invention may be practiced otherwise than as specifically described herein.

What is claimed as new and is desired to be secured by letters patent of the United States is:

1. A process for separating n-butyl chloride from a composition comprising n-butyl chloride and other isomeric $C_4$ alkyl chlorides, $C_1$–$C_3$ alkyl chlorides, $C_1$–$C_4$ alcohols, ethers, ketones, nitrites, and organo-sulfur compounds, comprising:

a) distilling the composition comprising at least 90% by weight of n-butyl chloride, at least one other isomeric $C_4$ alkyl chloride, at least one $C_1$–$C_3$ alkyl chloride, at least one $C_1$–$C_4$ alcohol, at least one ester, at least one ketone, at least one nitrile, and at least one organo-sulfur compound, to produce a condensed product or distillate having an enriched content of the n-butyl chloride as compared to the composition; and distillation bottom phase comprising high-boilers;

b) cooling the distillate, and c) washing the cooled distillate in a plurality of stages comprising washing with water followed by washing with dilute solution of an alkali metal hydroxide in water or washing with dilute solution of an alkali metal hydroxide in water followed by washing with water.

2. The process of claim 1, wherein the composition comprises at most 0.2% by weight of at least one other isomeric butyl chloride, at most 1% by weight of at least one $C_1$ to $C_3$ alkyl chloride, at most 8% by weight of at least one $C_1$ to $C_4$ alcohol, at most 3% by weight of at least one ester, at most 3% by weight of at least one ketone, and at most 0.5% by weight of at least one nitrile, and at most 0.1% of at least one organic sulfur compounds.

3. The process of claim 1, wherein the composition comprises 92 to 97% by weight of the n-butyl chloride, at most 0.2% of the at least one other isomeric butyl chloride, 0.1 to 0.5% by weight of the at least one $C_1$ to $C_3$ alkyl chloride, 2 to 6% of the at least one $C_1$ to $C_4$ alcohol, 0.01 to 2% by weight of the at least one ester, 0.01 to 2% by weight of the at least one ketone, and 0.01 to 0.1% by weight of the at least one nitrile, and 0.001 to 0.005% of at least one organic sulfur compound.

4. The process of claim 1, wherein the distilling step is conducted at a temperature of 50 to 120° C. and a pressure of 0.5 to 3 bar.

5. The process of claim 1, comprising 2 to 8 separate washing steps.

6. The process of claim 1, comprising 3 to 5 separate washing steps.

7. The process as claimed in claim 1, wherein the solution of an alkali metal hydroxide in water contains 1 to 5% by weight of sodium hydroxide.

8. The process of claim 1, wherein the at least one ester is at least one member selected from the group consisting of methyl acetate, butyl formate and n-butyl acetate.

9. The process of claim 1, wherein the at least one ketone is at least one member selected from the group consisting of acetone, methyl ethyl ketone and 4-methyl-2-pentanone.

10. The process of claim 1, wherein the at least one nitrile is at least one member selected from the group consisting of acetonitrile and butyronitrile.

11. The process of claim 1, further comprising washing the cooled distillate with a 1 to 70% wt. % aqueous solution of $H_2O_2$ prior to washing with the dilute solution of the alkali metal hydroxide in water.

12. The process of claim 11, wherein the concentration of $H_2O_2$ is 10 to 30 wt. %.

* * * * *

UNITED STATES PATENT AND TRADEMARK OFFICE
CERTIFICATE OF CORRECTION

PATENT NO. : 6,093,286  
DATED : July 25, 2000  
INVENTOR(S) : Clemens Osterholt, et al.

Page 1 of 1

It is certified that error appears in the above-identified patent and that said Letters Patent is hereby corrected as shown below:

On the Title Page,
Item [57] the Abstract, line 3, "nitrites," should read -- nitriles, --.

Column 1,
Line 8, "nitrites," should read -- nitriles, --.
Line 44, "d-in-butyl" should read -- d-n-butyl --.

Column 2,
Lines 45 and 57, "nitrites," should read -- nitriles, --.

Column 3,
Lines 8 and 49, "nitrites," should read -- nitriles, --.
Line 52 "nitrites." should read -- nitriles. --.

Column 5,
Line 18, "nitrites," should read -- nitriles, --.

Signed and Sealed this

Twenty-fourth Day of July, 2001

*Attest:*

*Attesting Officer*

NICHOLAS P. GODICI
*Acting Director of the United States Patent and Trademark Office*